United States Patent [19]

Cella et al.

[11] 4,176,176

[45] Nov. 27, 1979

[54] HAIR SHAMPOO AND CLEANSER COMPOSITIONS

[75] Inventors: John A. Cella, Plandone Mills, N.Y.; August E. Fiebig, Jr., Chicago, Ill.

[73] Assignee: Alberto-Culver Company, Melrose Park, Ill.

[21] Appl. No.: 474,955

[22] Filed: May 31, 1974

[51] Int. Cl.$^2$ .............................................. A61K 7/06
[52] U.S. Cl. ......................... 424/70; 252/DIG. 13; 252/545; 252/547; 252/548; 252/550; 424/DIG. 4; 424/311; 424/313; 424/315; 424/317; 424/321; 424/343
[58] Field of Search ............... 424/70, 311, 313, 315, 424/224, 317, 321, 343, DIG. 4; 252/545, 547, 548, 550, DIG. 13; 260/556 F

[56] References Cited

U.S. PATENT DOCUMENTS

| | | | |
|---|---|---|---|
| 2,732,398 | 1/1956 | Brice et al. | 260/556 F X |
| 2,759,019 | 8/1956 | Brown et al. | 260/556 F |
| 2,803,656 | 8/1957 | Ahlbrecht et al. | 260/556 F |
| 2,809,990 | 10/1957 | Brown | 260/556 F X |
| 2,915,554 | 12/1959 | Ahlbrecht et al. | 260/556 F |
| 3,147,064 | 9/1964 | Brown et al. | 8/116.2 |
| 3,436,262 | 4/1969 | Crowe et al. | 134/10 |
| 3,568,685 | 3/1971 | Scott | 424/71 X |
| 3,585,145 | 6/1971 | Fethke | 252/99 |

OTHER PUBLICATIONS

Schwartz et al., vol. 2, Surface Active Agents and Detergents, Interscience Publishers, New York, (1958), pp. 150–152.

*Primary Examiner*—James O. Thomas, Jr.
*Assistant Examiner*—Vera C. Clarke
*Attorney, Agent, or Firm*—Wallenstein, Spangenberg, Hattis & Strampel

[57] ABSTRACT

Hair shampoos and cleansers containing distinctly minor proportions of hydrophobic-lipophobic perfluorinated compounds.

6 Claims, No Drawings

HAIR SHAMPOO AND CLEANSER COMPOSITIONS

Our invention is directed to improved hair shampoo and cleansing compositions for keratinaceous fibers, especially hair on human heads.

It has long been known that the sebaceous glands in the human scalp substantially continuously secrete sebum which acts to keep the hair lubricated, smooth and shiny. It has also long been known that many people suffer from an overproduction of sebum and, as a result, have oily hair. Oily hair readily picks up dust and other particulate matter from the environment which results in the hair becoming soiled and sticky, a situation which requires frequent hair shampooing, commonly as often as every day or every other day, in order to make the hair look clean and presentable.

The secretion products of the sebaceous glands, especially if produced in excess, frequently have an adverse effect on certain hair care products which are applied to the human hair to impart desirable properties thereto in relation to texture, hold and general appearance. Among such hair treatment products, hair setting lotions, gels, hair conditioning products and hair sprays are most generally adversely affected by the sebum or natural oils secreted by the sebaceous glands. In this connection, it may be noted that such hair treatment products commonly contain resins or resinous ingredients, for instance, polyvinylpyrrolidone (PVP). The sebum or natural oils tend to plasticize the resins with the result that the desired properties of the resins are adversely affected, resulting in diminishing or loss of the holding power of the resins. The adverse effect of the sebum or natural oils secreted by the sebaceous glands is not, however, limited only to those hair treatment compositions which contain resins or resinous materials as ingredients thereof. Hair treatment compositions which impart to the hair such properties as body, sheen and a soft, silky touch, and which do not contain resins or resinous materials, are also commonly undesirably affected by reason of the spread of the sebaceous secretions along the hair shaft with the result that the hair becomes oily and sticky, depending upon the amount or extent of such secretions, measured, also, of course, as a function of time. In many instances it can be observed that resins or other materials deposited on hair speed up the spreading of the sebum along the hair shaft and, so, enhance the adverse effects of excess sebum.

We have found, in accordance with our present invention, that the incorporation into hair shampoos or hair cleansers of distinctly minor amounts of certain compounds not only does not adversely affect the effectiveness of the cleansing of the hair by said hair shampoos or hair cleaners but, indeed, enhances their effectiveness in that it substantially reduces the excess flow of the sebum or sebaceous secretions upon cleaning the hair with said shampoos. By doing so it maintains the properties and utilities of hair treatment compositions, which would adversely be effected upon contact with sebum. Shampooing, in general, particularly when done repeatedly and over relatively short intervals of time, afflicts certain damage to hair. The application of the shampoos of our invention keeps the hair less oily for a longer time and, by doing so, reduces the necessity of frequent shampooing.

The aforementioned chemical compounds which are incorporated into the hair shampoos or hair cleansing compositions to produce the hair shampoos and hair cleansers of our present invention are hydrophobic-lipophobic perfluorinated chemical compounds which can be represented by the formula $$CF_3-(CF_2)_x(CH_2)_y-Z$$

where Z is a water or oil solubilizing group of either organic or inorganic character, x is an integer which is generally from 2 to 17, particularly from 7 to 11, and y is an integer from 0 to 4, and said compounds may be anionic, cationic, nonionic or amphoteric, depending upon the nature of the grouping or groupings encompassed by Z. The Z groups may be or may comprise sulfonic, sulfate, phosphate, amide, alkyl-substituted amide, sulfonamido, carboxylic, quaternary ammonium, betainic and similar groups. The hydrophobic-lipophobic perfluorinated compounds are per se known to the art and are identified by trademarks such as the FLUORADS (Minnesota Mining and Manufacturing Company) or ZONYLS (E. I. du Pont de Nemours & Company). The water-solubility and organic solvent solubility of the aforesaid compounds are, as is known, affected and can be controlled by varying the chain length of the perfluorinated hydrocarbon moiety and by the selection of Z as designated in the above-mentioned formula.

Illustrative examples of the hydrophobic-lipophobic perfluorinated compounds are the following:

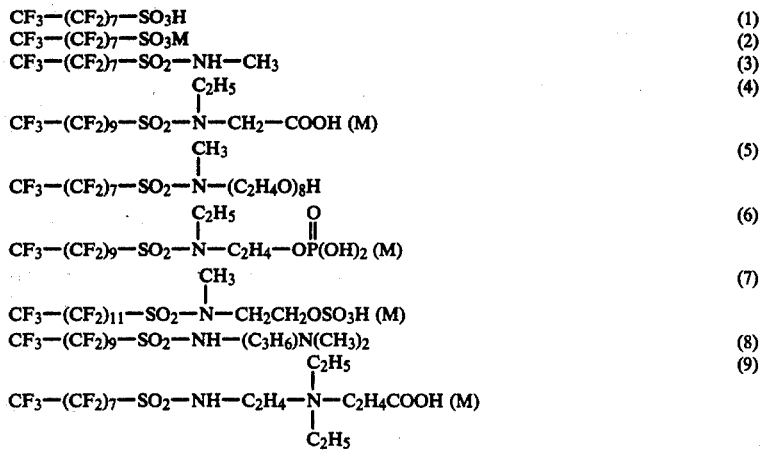

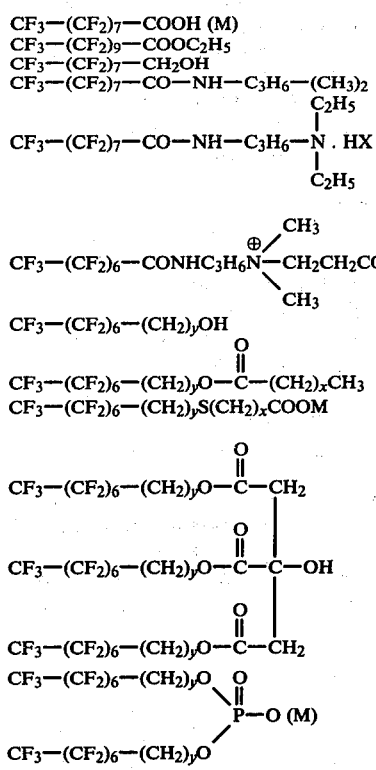

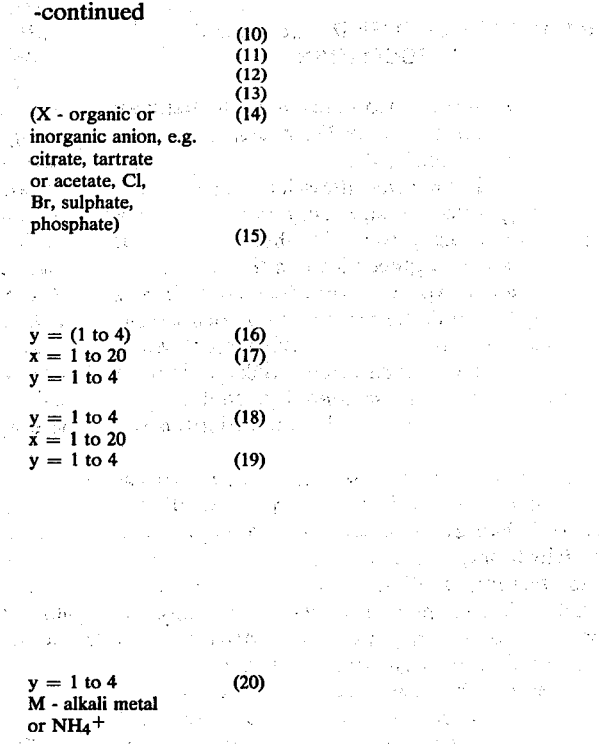

The aforesaid hydrophobic-lipophobic perfluorinated compounds are effective, in the hair shampoos or hair cleansers of our present invention, in very low concentrations, as low as 0.05%, by weight of the hair shampoos or hair cleansers, to of the order of about 1% or 2% or slightly higher. As a general rule, proportions of the order of about 0.1% to 1% are generally adequate, with a good general average being about 0.5% to 1%. The lower limit is determined by the particular efficacy of the specific compounds in selected hair shampoos or hair cleansers, whereas the upper limit, not in excess of 10%, is usually governed by somewhat similar considerations except that, generally speaking, no more should be used than is necessary and, in addition, it is desirable not to exceed the solubility or ready dispersibility limits of the compound in the particular hair shampoos or hair cleansers involved, while maintaining homogeneity therein. The hydrophobic-lipophobic perfluorinated compounds selected for use should be chosen, of course, so that they are compatible with the particular active detergent and other ingredients of any particular hair shampoo or hair cleanser composition.

The active detergent ingredients of the hair shampoos or hair cleansers containing the perfluorinated hydrophobic-lipophobic compounds may be water-soluble soaps, or non-perfluorinated anionic, cationic, (including Zwitterionic), amphoteric or nonionic detergents. The aforesaid soaps and non-perfluorinated detergents, which are generally and desirably of water-soluble character, are well known to the art and are commonly used in shampoo compositions. They include, by way of illustration, coconut oil fatty acids or oleic acid alkali metal or ammonium or amine soaps, water-soluble lauryl sulfate salts, usually alkali metal, ammonium and ethanolamine, commonly diethanolamine or triethanolamine, salts; alkanolamine salts of linear $C_{12}$–$C_{15}$ alkyl benzene sulfonic acids; water-soluble polyethoxylauryl alcohol sulfate salts; linear alkyl benzene polyoxyethyl sulfonate salts; sulfated lauric acid monoglyceride salts; quaternary ammonium compounds such as cetyltrimethyl ammonium chloride; nonionic detergents such as octylphenoxypoly(ethyleneoxy)ethanol; and amphoteric detergents. No novelty is claimed in the selection of any of such soaps or non-perfluorinated detergents as they are well known to the art are readily available for use in the novel hair shampoo compositions of the present invention. Various of them are disclosed, for instance, in such U.S. Pat. as Nos. 3,533,955; 3,658,985; 2,897,178; 3,350,319 and 3,526,592.

The shampoos also commonly contain foam boosters or foam stabilizers which, likewise, per se, are well known to the art and are commonly utilized in hair shampoo formulations. Illustrative thereof are dialkylolamides of $C_8$–$C_{18}$ fatty acids, as, for instance, lauric or cocodiethanolamides which are represented by the formula R—CO—N—(CH$_2$—CH$_2$—OH)$_2$ where R-CO is a saturated fatty acid acyl radical of $C_8$–$C_{15}$ fatty acids, particularly lauric acid or myristic acid or mixtures of saturated fatty acids containing predominately from $C_{12}$ to $C_{14}$ fatty acids and commonly derived from coconut oil.

In certain cases, particularly in the case of dry shampoo formulations which are used in dry form to cleanse the hair, no soap or detergent is employed. Such dry shampoo formulations are known to the art and, commonly, they do not contain either soaps or synthetic detergents. They are also improved through the incorporation therein of the hydrophobic-lipophobic perfluorinated compounds disclosed above.

The pH of the hair shampoos or hair cleaners of the present invention will generally vary from about 6 to 9 but, in the usual case, the pH will range from about 5.5 to about 7.5.

Supplemental ingredients for particular purposes can also be incorporated such as polymers, combing aids, etc. The hair shampoos or hair cleaners of this invention may be liquids, gels, creams or dry powders.

The following examples are illustrative but in no way limitative of the invention since many other hair shampoos or hair cleansers can readily be made in light of the guiding principles and teachings contained herein. All percentages listed are by weight, unless otherwise specifically stated.

EXAMPLE 1

| | |
|---|---|
| Sodium Lauryl Sulfate (30%) | 40.00 |
| Lauric Diethanolamide | 4.00 |
| Compound of structure 6 | 1.10 |
| Perfume | 0.25 |
| Dowicil 200 | 0.20 |
| Soft Water | 54.45 |
| | 100.00 |

In the preparation of the hair shampoo of this Example 1, it is convenient to heat the water to 130° F., then add the sodium lauryl sulfate and, with agitation, the lauric diethanolamide. The compound of structure 6 is then added and the resulting mixture is then allowed to cool to about 120° F. The Dowicil 200 is then added, with stirring, and when the mixture has cooled to about 100° F., the perfume is added. Stirring is discontinued when about ambient temperature is reached.

Mixing procedures for preparing other hair shampoo formulations of the present invention, illustratively disclosed in the following Examples, will be apparent to those skilled in the art.

EXAMPLE 2

| | |
|---|---|
| Water (Deionized) | 58.56 |
| Polymer JR-400[1] | 1.00 |
| Polymer JR-30M[1] | 0.50 |
| Triethanolamine Lauryl Sulfate | 37.00 |
| Lauric Diethanolamide | 2.00 |
| Methyl Paraben[2] | 0.10 |
| Compound of structure 6 | 0.84 |
| | 100.00 |

[1]Cationic cellulose derivative
[2]Para-Hydroxy Methyl Benzoate

EXAMPLE 3

| | |
|---|---|
| Cocodiethanolamide | 2.00 |
| Ammonium Lauryl Sulfate (30%) | 12.75 |
| Sodium Polyethoxylauryl Alcohol Sulfate (60%) | 12.00 |
| Chemadene 300[3] | 2.25 |
| Sodium Chloride | 3.25 |
| Polymer JR-30M | 0.60 |
| Soft Water | 65.95 |
| Dowicil 200[4] | 0.10 |
| Methyl Paraben | 0.10 |
| Compound of structure 20 | 1.00 |
| | 100.00 |

[3]Amphoteric surfactant
[4]1-(3-Chlorallyl)-3,5,7-Triaza-1,1-Azoniaadamantane

EXAMPLE 4

| | |
|---|---|
| Cocodiethanolamide | 2.00 |
| Ammonium Lauryl Sulfate (30%) | 14.50 |
| Sodium Polyethoxylauryl Alcohol Sulfate (60%) | 10.00 |
| Chemadene 300 | 2.25 |
| Sodium Chloride | 3.40 |
| Polymer JR-30M | 0.60 |
| Dowicil 200 | 0.20 |
| Compound of structure 6 | 0.82 |
| Soft Water | 66.08 |
| Perfume | 0.15 |
| | 100.00 |

EXAMPLE 5

| | |
|---|---|
| Water | 39.90 |
| Cetyltrimethyl Ammonium Chloride (25%) | 50.00 |
| Lauric Ethanolamide | 9.00 |
| Compound of structure 11 | 1.00 |
| Perfume | 0.10 |
| | 100.00 |

EXAMPLE 6

| | |
|---|---|
| Soft Water | 69.65 |
| Ethylene Glycol Monostearate | 1.00 |
| Polymer JR-30M | 0.60 |
| Miranol C2M-SF[5] | 21.00 |
| Standamid CD[6] | 2.00 |
| Polysorbate 80 | 2.00 |
| Lauryl Alcohol | 0.75 |
| Methyl Paraben | 0.30 |
| Citric Acid | 1.50 |
| Compound of structure 21 | 0.70 |
| Perfume | 0.50 |
| | 100.00 |

[5]Amphoteric surfactant
[6]Alkanolamide

EXAMPLE 7

| | |
|---|---|
| Igepal CA-630[7] | 15.00 |
| Cocodiethanolamide | 3.00 |
| Soft Water | 80.70 |
| Dowicil 200 | 0.10 |
| Methyl Paraben | 0.10 |
| Compound of structure 6 | 1.00 |
| Perfume | 0.10 |
| | 100.00 |

[7]Octylphenoxypoly(Ethyleneoxy)Ethanol

EXAMPLE 8

| | |
|---|---|
| Igepal CA-630 | 15.00 |
| Cocodiethanolamide | 3.00 |
| Dowicil 200 | 0.20 |
| Soft Water | 79.95 |
| Compound of structure 20 | 1.00 |
| Polymer JR-3 0M | 0.70 |
| Perfume | 0.15 |
| | 100.00 |

EXAMPLE 9

| | |
|---|---|
| Triton X-100[8] | 13.00 |
| Lauric diethanolamide | 2.50 |
| Soft Water | 82.60 |
| Methyl Paraben | 0.20 |
| Polymer JR-30M | 0.60 |
| Compound of structure 6 | 1.00 |
| Perfume | 0.10 |
| | 100.00 |

[8] Nonylphenoxy Polyethoxyethanol

EXAMPLE 10

| | |
|---|---|
| Starch | 4.00 |
| Ethanol | 6.00 |
| Compound of structure 19 | 1.00 |
| Propellant | 89.00 |
| | 100.00 |

The term "shampoo," as used in the claims, is intended to cover shampoos and cleansers for the washing or cleansing of hair, particularly hair on the human head.

We claim:

1. A hair shampoo in liquid or paste form for use on human hair attached to the human head which includes a water carrier, a non-perfluorinated water-soluble quaternary ammonium compound detergent, and which contains, as an additional ingredient thereof, a hydrophobic-lipophobic compound of anionic, cationic, nonionic or amphoteric character, corresponding to the formula $$CF_3-(CF_2)_x-(CH_2)_y-Z$$

where Z is a member selected from the class consisting of a water-solubilizing group and an oil-solubilizing group, x is an integer from 2 to 17, and y is an integer from 0 to 4, said compound being present in proportions, based on the weight of the shampoo, in the range of about 0.5% to about 2%, said compound being present in proportions less than the proportions of said detergent.

2. The shampoo of claim 1, in which the detergent comprises cetyltrimethyl ammonium chloride.

3. The shampoo of claim 1, in which, in the hydrophobic-lipophobic compound, x is 7 to 11, and in which the hydrophobic-lipophobic compound is a cationic compound.

4. The shampoo of claim 1, in which x is 7 to 11, and the hydrophobic-lipophobic compound is an amphoteric compound.

5. The shampoo of claim 1, in which x is 7 to 11, and the hydrophobic-lipophobic compound is a nonionic compound.

6. A hair shampoo in liquid or paste form for use on human hair attached to the human head which includes a water carrier, a non-perfluorinated detergent which is an alkali metal, ammonium or ethanolamine lauryl sulfate salt; lauric diethanolamide; and, as an additional ingredient of said hair shampoo, a hydrophobic-lipophobic compound of anionic, cationic, nonionic or amphoteric character corresponding to the formula $$CF_3-(CF_2)_x-(CH_2)_y-Z$$

where Z is a member selected from the class consisting of a water-soluble group and an oil-solubilizing group, x is an integer from 2 to 17, and y is an integer from 0 to 4, said compound being present in proportions, based on the weight of the shampoo, in the range of about 0.05% to not in excess of 10%, said compound being present in proportions less than the proportions of said detergent.

* * * * *